United States Patent [19]

Lentsch

[11] 4,258,056

[45] Mar. 24, 1981

[54] CONTROL OF MASTITIS AND COMPOSITIONS THEREFOR

[75] Inventor: Steven E. Lentsch, St. Paul, Minn.

[73] Assignee: Economics Laboratory, Inc., St. Paul, Minn.

[21] Appl. No.: 31,429

[22] Filed: Apr. 19, 1979

Related U.S. Application Data

[63] Continuation-in-part of Ser. No. 970,653, Dec. 18, 1978, which is a continuation-in-part of Ser. No. 880,335, Feb. 23, 1978, abandoned.

[51] Int. Cl.$^3$ .................. A61K 31/255; A61K 31/24
[52] U.S. Cl. ..................................... 424/303; 424/309
[58] Field of Search .............................. 424/303, 309

[56] References Cited

U.S. PATENT DOCUMENTS

| | | | |
|---|---|---|---|
| 2,474,412 | 6/1949 | Bersworth | 252/106 |
| 2,506,492 | 5/1950 | Mytt et al. | 424/71 |
| 2,717,243 | 9/1955 | Bloch | 252/539 |
| 2,806,789 | 9/1957 | Kiser et al. | 424/227 |
| 2,904,468 | 9/1959 | Davis et al. | 424/315 |
| 3,141,821 | 7/1964 | Compeau | 424/65 |

*Primary Examiner*—Delbert R. Phillips
*Attorney, Agent, or Firm*—Merchant, Gould, Smith, Edell, Weiter & Schmidt

[57] ABSTRACT

Neutral to mildly acidic externally-applied mastitis control agents comparable to iodophor teat dips in activity can be obtained from the combination of an anionic surfactant (e.g. an aromatic sulfonate or sulfonic acid) and an aminocarboxylic-type chelating agent. A nitroalkanol antibacterial can be included in the composition. The full strength teat dip contains a major amount of water (but less than 98%) and typically includes an emollient, a buffering agent, and a thickener. The anionic surfactant (which is believed to be effective against gram positive mastitis-causing organisms) and the chelating agent appear to cooperate in the pH range above 4 and below 7. The chelating agent is believed to improve the cell wall permeability of the mastitis-causing organisms, even in this pH range.

13 Claims, No Drawings

CONTROL OF MASTITIS AND COMPOSITIONS THEREFOR

This application is a continuation-in-part of my co-pending application Ser. No. 970,653, filed Dec. 18, 1978, which in turn is a continuation-in-part of my application Ser. No. 880,335, filed Feb. 23, 1978, which is now abandoned.

TECHNICAL FIELD

Milking of cows on a large scale is almost entirely done with a milking machine. The milking machine draws the milk from the cow's udder by pulsating vacuum, e.g. by attaching a teat cup connected to a vacuum pump and pulsating the vacuum to alternately allow the milk to fill and drain from the area of the udder and teat to simulate hand milking of the cow. The tendency is to minimize the milking time by using high vacuum which causes irritation to the teat and udder.

The milk secreted through the teat canal is essentially sanitary. However, contamination of the teat environment is virtually unavoidable under normal field conditions, even when sanitized milking equipment is used. A wide variety of microorganisms can be present on or near the cow's udder and may even enter the teat canal, thus creating the possibility of infection.

The damage to tissue caused by the milking machine followed by exposure of the damaged tissue to certain microorganisms can result in an infection known as mastitis. This problem is of great economic importance to the dairy farmers because the infected cow's contaminated milk cannot be marketed. The infected udder must be treated with an antibiotic. However, the milk from such cows cannot be sold until the antibiotic is absent from the milk (usually about 3–5 days after the last treatment with the antibiotic.

According to experts, the dipping of teats in an antimicrobial (biostatic or biocidal) solution after milking is one of the most effective procedures that a dairy farmer can follow to prevent infections of the udder. An essential purpose of the teat dip is to prevent mastitis by killing or controlling the microorganisms and permitting injured tissue to heal. The teat dip product desirably has a broad spectrum of antibacterial activity to minimize infection, typically has emollient properties to promote healing and typically is or can be buffered to approximate "skin" pH, thereby minimizing irritation possibilities. Ideally, the spectrum of activity should include gram negative as well as gram positive organisms, although most cases of bovine mastitis are believed to be caused by gram positive bacteria.

PRIOR ART

A number of teat dip products or mastitis control agents are available to dairy farmers which have varying degree of effectiveness. These products or agents have in common an antimicrobial or sanitizing agent which is an active ingredient (usually the principal active ingredient) of the treating solution. Prior art formulas typically include agents which are effective against gram positive microorganisms such as *Staphylococcus aureus* and *Streptococcus agalactiae*.

The following references are believed to be illustrative of published scientific and patent literature regarding teat dips:

British Pat. No. 1,144,637 (Kilco Chemicals, Ltd.), published Mar. 5, 1969.

U.S. Pat. No. 3,993,777, issued Nov. 23, 1976.
U.S. Pat. No. 4,025,628, issued May 24, 1977.
"Modern Teat Dips", appearing in *The Veterinary Record*, Vol. 93 (No. 133), Dec. 15, 1973.
Philpot et al, *J. Dairy Science*, 58(a):209.

As will be apparent from these references, numerous antimicrobial agents have been investigated, including iodophors, PVP-iodine (a particular iodophor), hypochlorites, chlorine dioxide, chlorinated isocyanurates (chlorinated-S-triazene-trione), bromine, hydroxyquinoline, ammonium chloride, chlorhexidine, hexachlorophene, diaphene, cetyl pyridinium chloride, and the quaternary ammonium germicides disclosed in the aforementioned U.S. Pat. No. 3,993,777. Of the topically applied agents which have been investigated for control of bovine mastitis, iodophors, quaternary ammonium compounds, and chlorine-releasing sanitizing agents (particularly sodium hypochlorite and, more recently, chlorinated isocyanurates) presently appear to have gained the widest acceptance among dairy farmers, despite the fact that some of the chlorine-releasing sanitizers (e.g. 4% aqueous NaOCl) can have an irritating effect upon cow teats. (The irritation can be mitigated with emollients but may still occur.) And, at this stage of commercial development of the iodophors, there is some concern on the part of researchers who believe that this sanitizing agent may be capable of contaminating the milk. Teat dips of the future may have to be iodine-free.

An iodine-free teat dip which appeared in the marketplace fairly recently is sold under the "SURGE" trademark by the Babson Brothers Company of Oakbrook, Illinois, U.S.A. According to the "SURGE" label, this teat dip contains lauryl-poly-1-oxypropene, ethoxylated sterols and ethoxylated lipids, propylene glycol, and, presumably as its principal active ingredient, the antimicrobial agent 2-bromo-2-nitropropane-1,3-diol.

It is known in the art that linear alkylbenzene sulfonates or linear alkylbenzene sulfonic acids are moderately effective bactericides, particularly in acid mediums. For example, they can be active against gram positive organisms such as *Staphylococcus aureus*. However, a high level of a linear alkylbenzene sulfonate may be undesirable for use in a teat dip product because it may defat the tissue and promote skin irritation.

The effect of chelating agents such as ethylene diamine tetra-acetic acid (EDTA), on certain bacteria has been studied. For example, in an article entitled "The Effect of Ethylene-diaminetetra-acetic Acid on the Cell Walls of Some Gram-Negative Bacteria" by G. W. Gray and S. G. Wilkinson, published in *The Journal of General Microbiology*, Volume 39, p. 385 (1965), the authors disclose that EDTA had a lytic bactericidal action on *Pseudomonas aeruginosa*. By treating the cell walls of *Pseudomonas aeruginosa* with a 0.003 M solution of EDTA and a borate buffer of pH 9.2 for one hour at 18°–20° C., the authors found that the turbidity of the aqueous suspensions of the walls was substantially decreased (about 30%). (See pages 386 and 394.) In an article entitled "Effect of Ethylenediaminetetra-acetic Acid and Related Chelating Agents on Whole Cells of Gram-Negative Bacteria" by H. Haque and A. D. Russell published in *Antimicrobial Agents and Chemotherapy*, Vol. 5, No. 5, pp. 447–452, May 1974, the authors found that EDTA dissolved in a borate buffer of pH 7.8 or 9.2 was fairly effective in reducing the viability of two strains of *Pseudomonas aeruginosa* when treated for fairly long periods of time, i.e. 30–60 minutes. The authors also noted that the bactericidal effect of EDTA was greater at pH 9.2 than at pH 7.8. (See pages 447-449.)

The effect of chelating agents such as EDTA (and various other aminocarboxylic-type chelating agents) on the susceptibility of certain strains of bacteria to certain antibacterial agents has also been studied. In an article entitled "Effective Chelating Agents" written by H. Haque and A. D. Russell published in *Antimicrobial Agents and Chemotherapy*, Vol. 6, page 200 (August 1974), the authors disclose that pretreatment with a chelating agent such as EDTA increased the susceptibility of two strains of *Pseudomonas aeruginosa* to the antibacterial action of cetrimide, chlorhexidine, and benzalkonium chloride when treated for relatively long periods of time, i.e. 30-60 minutes. Besides EDTA, the other aminocarboxylic-type chelating agents studied by the authors were cyclohexane-1,2-diaminetetraacetic acid (CDTA), N-hydroxyethylethylenediaminetriacetic acid (HEDTA), iminodiacetic acid (IDA), and nitriloacetic acid (NTA, sometimes called nitrilotriacetic acid). The authors also disclose that pretreatment with EDTA increased the susceptibility of the foregoing two strains to β-lactam antibiotics, in particular carbenicillin, but not as much as with respect to the other antibacterial agents when exposed for relatively long periods of time, i.e. 30-60 minutes. In order to carry out the pretreatment process, the authors suspended the particular strain of bacteria in a "Tris" buffer of pH 7.8 ("Tris" is tris[hydroxymethyl]aminomethane) added to a Tris-buffered solution of EDTA having a pH of 9. The authors then added the EDTA solution with bacteria to a solution of a particular antibacterial agent or antibiotic previously equilibrated at 37° C. After addition to the antibacterial or antibiotic solution, the mixture was incubated at 37° C. Samples were removed immediately and at 30, 45 and 60 minutes for determination of the number of viable cells per milliliter or in the case of the antibiotic, immediately and at 30 and 60 minutes.

As compared to biocides or biostatic agents generally, the testing of experimental teat dip products in the laboratory poses many problems. Some tests, while valid for determining inhibitory concentrations of antibacterial substances, do not indicate whether the organisms are killed or merely prevented from multiplying. For many uses such as preserving of pharmaceuticals, shampoos, etc. such testing is believed to be a perfectly valid method of screening antimicrobial agents. However, a minimum inhibitory concentration is generally much lower than a killing concentration. Often there is a lack of correlation between the two figures in comparing different antimicrobial agents. That is, two antibacterial substances which have approximately the same minimum inhibitory concentration may differ widely in their killing concentration. Thus, depending on the intended use and purposes, both the minimum inhibitory concentration and the killing concentration must be determined to give a guide to a meaningful use-concentration. In a topical application such as a teat dip product (as against intramuscular injection), killing the organism is ordinarily considered much more effective in preventing infection than merely inhibiting the organism.

Furthermore, the control of bovine mastitis requires rapid high rates of kill, since prolonged treatment (e.g. more than 15 minutes or even more than a minute) with the teat dip is normally impractical. Bactericidal tests of teat dip formulas should be conducted with a view toward measuring the short-term kill. Perhaps more important, field studies and field experience with known bactericidal teat dip compositions tend to indicate that in vitro testing of the bactericidal effect is not always particularly informative. Some studies suggest that the interior of the teat canal can be infected, and bacteria can multiply very easily in this very hospitable site for microorganism growth. Milk or milk residues in the teat canal or other infected sites can provide a nutrient medium. To make in vitro testing more realistic, milk (e.g. skim milk) is sometimes added to the in vitro growth medium. Another approach to greater reliability for measuring bacteriostasis and/or kill rates is the "semi-in vivo" test, wherein preserved, excised teats collected from a slaughterhouse are dipped in a suspension of colony forming units and later treated with the teat dip. The more realistic tests sometimes suggest that an excellent in vitro kill may correlate poorly at best with effectiveness in the field. Field studies are, in the final analysis, the most definitive, but the semi-in vivo test can, according to some experts, be a reasonable approximation of actual use.

SUMMARY OF THE INVENTION

It has now been discovered that a relatively concentrated, buffered, skin-pH solution of a common anionic surfactant or detergent and a water soluble aminocarboxylic acid or aminocarboxylate chelating agent has about the same or better activity against the more virulent gram positive mastitis-causing organisms (such as *S. aureus* and *S. agalactiae*) as the more commonly used, but relatively more exotic, teat dip biocides and biostats. No significant adverse effect upon teat skin has been observed in field tests in which the buffered anionic surfactant/chelating agent composition was combined with an emollient. Other known teat dip biocides or bacteriostats, preferably iodine-free (e.g. a nitroalkanol such as 2-bromo-2-nitropropane, see Clark et al, U.S. Pat. No. 3,558,788, issued Jan. 26, 1971) can be included in the composition for their known activity against gram negative organisms and/or gram positive organisms and/or spoilage organisms. The chelating agents found to be effective have a calcium chelate stability constant of at least about 6, the preferred chelating agent being a water soluble ethylenediamine tetraacetic acid salt, hereinafter referred to as an EDTA salt.

Accordingly, this invention contemplates a topically applied composition for the treatment of mastitis, and topical application by the conventional teat dip technique is preferred. Various conventional teat dip ingredients, such as water thickeners or thixotropes, are preferably included in the composition; as noted previously, the composition is preferably also buffered and provided with an emollient.

Topical mastitis-treating compositions of this invention, according to available test results, appear to provide relatively quick bactericidal action, e.g. an effective kill in 15 to 30 seconds. Furthermore, compositions according to the present invention have been found to have excellent activity against the virulent gram positive mastitis-causing organisms under neutral or mildly acidic conditions, e.g. a pH of 4 to 7, more preferably below 6.5. The anionic detergent appears to insure adequate activity against gram positive organisms at a pH below 7.

The constituents of the present invention can be prepared in "dry form" and later added to water to form an aqueous solution; however, it is preferred to mix the ingredients with a major amount of water (but less than about 98% by weight) to provide an aqueous solution in which the active ingredients are at the "use" concentration.

DETAILED DESCRIPTION

In this application, the following terms have the indicated meanings:

"Uniformly distributable" means soluble or dispersible.

"EDTA" means ethylenediamine tetraacetic acid.

"EDTA salt" means a chemical compound in which one or more replaceable hydrogens or hydrogen cations of EDTA (i.e. the protons of the four —COOH groups which theoretically would be released by the reaction —COOH→—COO$^\ominus$+H$^\oplus$) have been replaced by a different cation, e.g. an alkali metal cation. The term "EDTA salt" is intended to include both preformed salts, which are blended with the other ingredients of compositions of this invention, and EDTA salts formed in situ, e.g. from the reaction of EDTA itself and alkali metal hydroxides or basic salts.

"EDTA$^{-4}$" means the ethylenediamine tetraacetate anion, i.e. the anion resulting when all the protons have been removed from all four carboxyl groups of the EDTA molecule.

"Bactericidal" means that the organism is killed as opposed to the term "bacteriostatic" which means that the growth of the organism is inhibited.

COMPONENTS USED IN THE COMPOSITIONS OF THIS INVENTION

As noted previously, compositions of this invention are typically "teat dips" and will be described as such, though, of course, other methods of topical application besides teat-dipping such as spraying might be used, if equally effective in killing bacteria. The anionic surfactants, EDTA salts and other aminocarboxylic-type chelating agents, other non-iodine biocides or bacteriostats, emollients, thickeners, and buffers of a typical teat dip will now be described in detail.

It presently appears that, if the anionic surfactant is omitted from compositions of this invention, activity against gram positive microorganisms is sacrificed, including short-term kill of some of the more virulent gram positive mastitis-causing bacteria (e.g. *S. aureus*). The anionic surfactant tends to have maximum biocidal activity and/or biostatis at a pH below 7 and hence can be added to the composition in the acid form. For reasons which are presently not understood, the EDTA salt and the anionic surfactant cooperate very effectively at mildly acidic pH's. It might be expected that there would be no mutually effective pH for both the anionic surfactant and the EDTA, but experiments conducted with this invention do not presently confirm any such difficulty with the pH range.

Preferred anionic surfactants have the formula $$LSO_x{}^\ominus N^\oplus$$

wherein L is organic, typically an aromatic or aliphatic radical (including alkyl-aryl radicals), x is 3 or 4, and N$^\oplus$ is a topically acceptable cation such as a proton, an alkali metal cation, ammonium, or organic ammonium (e.g. triethanolammonium), an alkali metal cation or a proton being preferred. The preferred aromatic or aliphatic radicals are the linear alkyls and linear alkyl-aryls. All anionic surfactants do not work with equal effectiveness, and linear alkylbenzene sulfonates presently appear to provide very adequate activity against *S. aureus* and the like at a pH near 5.

With respect to the linear alkyl chain, it should not be so long as to create incompatibility with water yet not so short so that skin irritation can become a problem. Therefore, the alkyl chains should preferably be 9 to 18 carbons in length. All sulfonates are not equally effective, the most preferred linear alkyl benzene sulfonic acid salt for use in connection with compositions of the present invention being sodium dodecylbenzenesulfonate. As is known in the art, the $C_{12}$ benzene sulfonates and the corresponding sulfonic acid are commercially available as mixtures with the $C_{14}$ and $C_{16}$ homologs and sometimes other homologs as well. The degree of purity of the $C_{12}$ species does not appear to be important in the context of this invention, and commercially available forms of the sulfonic acid and its salts are fully useful, without purification.

Water soluble EDTA salts preferred in practicing the present invention are represented by the formula $$EDTA^{-4}H_m{}^\oplus M_{4-m}{}^\oplus$$

wherein EDTA$^{-4}$ is ethylenediaminetetraacetate, M+ is a topically acceptable cation such as an alkali metal or ammonium cation, and m is an integer from 0 to 3. Preferably, M+ is sodium or potassium with the most preferred EDTA salt being EDTA$^{-4}$H$_2{}^\oplus$Na$_2{}^\oplus$, although other sodium EDTA salts are commercially available, including the tetra sodium salt. The amount of the EDTA salt added to the composition according to the present invention should be sufficient to significantly increase the short-term topical bactericidal effect of the teat dip. Preferably, this amount is sufficient to insure destruction of substantially all of the virulent mastitis-causing gram negative organisms on teat skin surfaces. In a composition useful as is for teat dipping, the EDTA salt comprises 0.1 to 4 or 5% and most preferably 1% by weight of the total composition (including water). It appears that the EDTA salt improves the permeability of the cell wall to bactericidal agents, including highly active anionic surfactants. Although this invention is not bound by any theory, it is believed that the permeability of the cell wall is improved due to the fact that the EDTA salt removes calcium ions from the cell wall.

When aqueous teat dips containing a major amount of water are made up according to this invention, the EDTA salt may be partially inactivated by hardness in the water. Under such circumstances, the amount of EDTA salt included in the composition will be in excess of the amount needed to chelate water hardness, so that a hardness-free aqueous medium containing free, unchelated ethylenediaminetetraacetate anions is obtained. Less than 1% by weight of EDTA salt will tie up all the hardness is typical "hard" waters; accordingly, a 1 to 4% by weight level of EDTA will have at least some effectiveness in this invention almost regardless of water hardness. Also believed to be of major importance is the calcium-rich residual milk remaining on the teat or in the test canal. This EDTA level will also tie up such calcium.

If tetrasodium or tetrapotassium EDTA is used as the EDTA salt, the buffer system (described subsequently) will ordinarily be designed to counter the pH-raising effect of such salts. Disodium EDTA has a much less pronounced pH-raising effect and is still sufficiently water soluble for use in the invention.

For the aforementioned theoritical reason, the M+ cation is monovalent. It is presently theorized that a polyvalent cation (particularly divalent cations such as those of the alkaline earth metals) could interfere with the chelating capacity of the EDTA salt. The chelate binding constant of EDTA/monovalent ion chelates can be very low—generally less than 5 and typically near zero. The EDTA/Ca chelate constant, on the other hand, is well above 5 (i.e. 10.6).

Since EDTA itself is only slightly soluble in water, its use in the present invention is not preferred, unless it is neutralized to an EDTA salt in situ, e.g. with an alkali metal hydroxide or a basic salt.

Water soluble aminocarboxylic-type chelating agents having a calcium chelate stability constant of at least about 6 (e.g. about 6 to about 13) appear to provide a "potentiating" effect similar to (and in some cases almost identical to) EDTA, though EDTA salts are still preferred for reasons of commercial availability, low toxicity, and wide acceptance in various arts such as the food and pharmaceutical arts. The preferred aminocarboxylic acid or aminocarboxylate chelating agents are at least tridentate, although, according to the scientific literature on bactericidal effects of aminocarboxylates, the bidentate iminodiacetic acid (IDA) should behave in a manner closely analogous to the tridentate nitrilotriacetic acid (NTA), one of the preferred chelating agents. At a pH below 7, it might be assumed that the —COO$^\ominus$ group is the most effective dentate substituent, and that hydroxyl-type dentates (e.g. of the hydroxyalkyl type) would be less effective; however, experimental data indicate that hydroxyaminocarboxylic or hydroxyaminocarboxylate chelating agents can be a fully effective type of aminocarboxylic or aminocarboxylate agent suitable for use in this invention, provided that the calcium stability constant is at least about 6. Surprisingly, however, the effectiveness of aminocarboxylic-type chelating agents in the context of this invention does not appear to depend entirely upon stability constants, since 3 to 5 minutes of treatment with a composition containing nitrilotriacetic acid (calcium stability constant=6.41) appeared to provide results comparable to aminocarboxylates having significantly greater calcium stability constants.

The aminocarboxylic-type chelating agents most effectively employed in this invention contain a substituted nitrogen atom or nitrilo group which is linked to the alpha carbon (alpha to the —COO$^\ominus$ substituent). In other words, the nitrogen atom typically has two or more monovalent acetic acid or ethanoate substituents (—CZ$_2$COO$^\ominus$, where Z can be H). A typical chelating agent of this type can be represented by the structural formula R—N(CH$_2$COO$^\ominus$)$_2$H$_a{}^\oplus$M$_{2-a}{}^\oplus$ wherein
R represents an organic residue,
a is 0 to 2, and
M+ is as defined previously.

The organic residue R can and preferably does contain additional aminocarboxylic-type chelating functionality, so that the chelating agent molecule will be at least tridentate in aminocarboxylic acids or aminocarboxylates. In the case of the bidentate IDA, R would be hydrogen; IDA is one of the most water soluble of the amino-carboxylic chelating acids. (As in the case of EDTA, the aminocarboxylic salts can be preformed or formed in situ by reaction with an alkali metal hydroxide or a basic salt.) Preferred examples of R are:

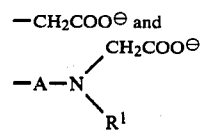

wherein
A represents a divalent aliphatic or cycloaliphatic nucleus or a polyalkylene polyamine chain such as diethylenetriamine, including diethylenetriamine substituted with further dentates (e.g. ethanoates), and R$^1$ is ethanoate (—CH$_2$COO$^\ominus$), lower hydroxyalkyl (e.g. —CH$_2$CH$_2$OH), or the like.

According to the scientific literature, chelating ability is not necessarily lost when organic groups (besides the nitrilo group) are substituted on the alpha carbon, i.e. —CH$_2$COO$^\ominus$ can be —CRHCOO$^\ominus$ or —CR$_2$COO$^\ominus$. For example, chelating agents such as N,N$^1$-ethylenebis-(2-o-hydroxyphenol)glycine have been synthesized, wherein the dentate is —NH—CH(PhOH)-COO$^\ominus$, Ph representing a phenyl group.

Besides EDTA, the common aminocarboxylic acids with calcium chelate formation constants greater than 6 are:

nitrilotriacetic acid (NTA),
hydroxyethylethylenediaminetriacetic acid (HEDTA),
cyclohexane-1,2-diaminotetraacetic acid (CDTA),
diethylenetriaminepentaacetic acid (DPTA), and
analogs of the foregoing such as triethylene tetramino polyacetic acids, other lower alkylene diamine tetraacetic acids (the term "lower" being understood to include carbon chains up to 6 carbons in length), analogs in which an acetic acid (ethanoate) dentate is replaced by a hydroxy-lower alkyl group, etc.

In other words, the preferred aminocarboxylic-type, polydentate chelating agents are the water soluble nitrilopolyacetic acids (and their water soluble salts) which have calcium chelate stability constants greater than about 6. Both mononitrilo- (e.g. NTA) and polynitrilo-polyacetic acids (e.g. EDTA, CDTA, HEDTA, DPTA, etc.) are operative in this invention, and the preferred polydentates are at least tridentate in chelating functional groups capable of chelating calcium in neutral and acidic media. Most typically, the nitrilopolyacetic acid, in its acetate form, contains the aminodicarboxylic or aminodicarboxylate bidentate grouping —N(CH$_2$COO$^\ominus$)$_2$, and preferably at least one additional aminocarboxylate or aminocarboxylic dentate.

Representative calcium and magnesium chelate constants (from Chaberek et al, *Organic Sequestering Agents,* John Wiley and Sons, N.Y., N.Y., 1959) are set forth below.

| Agent | Stability Constants | |
|---|---|---|
| | Ca$^{++}$ Chelate | Mg$^{++}$ Chelate |
| NTA | 6.41 | 5.41 |

| Agent | Stability Constants | |
|---|---|---|
| | $Ca^{++}$ Chelate | $Mg^{++}$ Chelate |
| EDTA | 10.59 | 8.69 |
| HEDTA | 8.0 | 5.2 |
| CDTA | 12.50 | 10.32 |

Although field testing of compositions of this invention, viewed in the light of results from laboratory in vitro tests appears to suggest that the anionic surfactant-/aminocarboxylate combination provides short-term kill of mastitis-causing gram positive organisms in mildly acidic test dip media containing less than about 98% by weight of water (e.g. 80–92% by weight), it may be desirable to include other biocides and/or biostatic agents in the test dip. Although this invention is not bound by any theory, it is believed that some of these additional agents can provide long-term post-treatment inhibition of the mastitis-causing organisms. The preferred additional antibacterials are preferably free of combined or uncombined iodine and titratable chlorine. It is believed that strong inhibitory or other antibacterial activity can be obtained through the use of the nitroalkanols disclosed in the aforementioned Clark et al patent.

Thus, nitroalkanols suitable for use in the present invention are represented by the formula

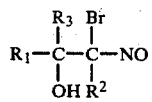

wherein $R_1$ is hydrogen, alkyl having 1 to 12 carbon atoms, and phenylalkyl of up to 10 carbon atoms, $R_3$ is hydrogen, or $R_1$ and $R_3$ together with the shared carbon atom form a cycloalkyl ring having 5 to 7 carbon atoms, and $R_2$ is hydrogen, methyl, ethyl, hydroxymethyl, or bromine. An extensive listing of nitroalkanols suitable for employment in antibacterial compositions according to the present invention and their properties can be found at column 1, line 31 to column 2, line 38 of the Clark et al U.S. Pat. No. 3,558,788, the disclosure of which is hereinafter incorporated by reference. All nitroalkanols are not equally effective, however, and the nitroalkanol most preferred in practicing the present invention is the nitroalkadiol 2-bromo-2-nitropropane-1,3-diol. In a composition useful as is for teat dipping, the amount of nitroalkanol used generally is within the range of 0.05 to 0.5% by weight of the total composition (including aqueous diluent medium). The optimum "use" concentration appears to be 0.15% by weight. Increasing the "use" concentration up to 0.5% may improve performance slightly, but will also increase costs. Beyond 0.5%, the improvement (if any) is believed to be not justified by the cost.

In those situations in which the activity of the nitroalkanol is not considered essential or even important to the effectiveness of the teat dip, there are advantages in omitting the nitroalkanol totally and relying upon the anionic detergent/aminocarboxylic chelate combination. First, the nitroalkanol is an expensive ingredient, particularly as compared to many highly effective anionic surfactants. Second, the amount of experience with the nitroalkanols in a veterinary or medical treatment or food production context is minimal as compared to the experience with alkyl-aryl sulfonates and EDTA. Compounds such as sodium dodecylbenzene sulfonate and its close analogs have been used in contexts involving contact with both human and animal skin for many years. EDTA has been used in foods and has been administered internally in the treatment of humans for many years also. The most widespread use of 2-bromo-2-nitropropane-1,3-diol has been in the preservative field (this compound is known to either inhibit or destroy a variety of spoilage-causing organisms).

Emollients incorporated into compositions of the present invention can serve to replace some of the natural skin oil lost by the milking process and/or to assist in forming a protective coating on the skin. An emollient which has a soothing action on teat skin, preferably by a humectant action; which is compatible with aqueous solutions of EDTA salts and antimicrobial brominated nitroalkadiols, such as 2-bromo-2-nitropropane-1,3-diol; and which does not significantly detract from the antimicrobial action of the active ingredients of the teat dip can be utilized in this invention. Liquid, oily organic emollients (e.g. polyols with relatively high boiling points, typically above 100° C. at 1 atmosphere) are preferred, but water soluble or water dispersible solids such as polyvinyl pyrrolidone or sorbitol have been used effectively in known teat dip formulas. Sorbitol takes up moisture under some conditions and is thus believed to provide an emollient action similar to liquid polyols. In addition to polyvinyl pyrrolidone (PVP) and the emollients used in the "SURGE" product cited previously, other well known emollients can be found at column 2, lines 30–43 of the patent to Caughman et al, U.S. Pat. No. 3,933,777, issued Nov. 23, 1976, the disclosure of which is incorporated by reference. All emollients do not work with equal effectiveness, and a preferred emollient for use in practicing the present invention is glycerine. The amount of the emollient in a composition suitable for use as is for teat dipping should be in the range of from 0.1 to 10%, most preferably about 8 to 10% by weight of the total composition (including aqueous diluent). Amounts up to about 20% by weight of emollient can be used (see U.S. Pat. No. 4,025,628, Table I) but such amounts are not believed to be necessary in the context of this invention. Another type of preferred emollient is the liquid anionic polyfunctional surface active agent sold under the trade name Rewoderm S-1333 (trade name Rewo Chemical, Incorporated, Farmingdale, L.I., New York, 11735, U.S.A.). This emollient is said to be effective for use with anionic surfactants. While the chemical nature of this product has not been disclosed, it is believed to be substantive to the skin and either prevents moisture loss or is a humectant or both. An emollient such as Rewoderm S-1333 is also an effective addition to the composition of the present invention.

As disclosed in U.S. Pat. No. 4,025,628, cited previously, powdered, storage stable water-soluble or water dispersible emollient-antimicrobial formulas can be mixed with water on the job to make an active teat dip. This procedure can avoid the need to ship a large amount of aqueous diluent to the end-user. However, it is preferred to prepare compositions of this invention in stable aqueous solutions in which the active ingredients are at the "use" level. Many dairy farmers purchase readily available laundry-type liquid bleaches (such as 4% aqueous sodium hypochlorite) and use them as concentrates for teat dipping—the common practice being to dilute the liquid laundry bleach with plain water prior to use. The practice of diluting a "concentrate" is not preferred in the context of this invention. It presently appears that the active ingredients of a teat dip made according to this invention are truly "active" (i.e. able to provide significant short-term kill of the aforementioned virulent gram positive organisms) only within a certain range of concentrations. Dilution of the teat dip beyond the "active" range, e.g. to the low "use" concentrations considered conventional for many hard surface cleaners (wall and floor cleaners, etc.) could render the active ingredients worthless or nearly worthless as teat sanitizers.

Water is suitable as a diluent in compositions of this invention, since commercially available aminocarboxylate salts (such as sodium salts) and suitable commercially available nitroalkanols (such as 2-bromo-2-nitropropane-1,3-diol) dissolve readily in water; furthermore, water has unquestionable economic advantages over organic liquid diluents. The preferred aqueous diluent used in this invention is water thickened with a thickening agent or thixotrope.

When compositions of this invention are prepared for distribution or sale at a concentration suitable for their end use (as is preferred), the water phase still makes up the major amount by weight of the total composition, even though the composition is relatively concentrated as compared to a typical hard surface cleaner diluted to its "use" concentration. Typically, more than 75% by weight of the composition will be water or other pharmaceutically inactive ingredients. In order to allow for at least about a percent by weight of emollient and at least about a percent by weight of buffers, thickening agents, and topically active agents such as the sulfonate, the EDTA salt, etc. it is preferred that the amount of water in the "use" concentration be less than 98% by weight. Typical amounts of water used in such end use concentrations range from about 80 to 95% by weight; if a full 8% by weight of emollient is used, the water content will be less than 92% by weight.

For typical teat dip applications, a liter (1,000 ml) of solution is a more-than-adequate amount to provide full immersion of the animal's teats in the dip, and an amount of solution within the range of 100–500 ml can be sufficient. It must be remembered that, if water is to be added to a concentrate or a dry formula, the pH of tap water can vary with hardness and other factors. Hard water with a pH approaching 10 is known, as is water with a pH on the slightly acid side. Softened, deionized, distilled, or neutral water is preferred for use in this invention, although a well-designed buffer system can take care of fluctuations in pH which might be introduced by slightly alkaline tap water. As will be apparent from the discussion of the function of the aminocarboxylic-type chelating agent, water containing calcium or magnesium "hardness" could have a minor but nevertheless detrimental effect upon the efficacy of the composition.

When a well-controlled product containing a fully effective aminocarboxylate/anionic surfactant combination is provided by selecting the appropriate amount of aqueous diluent and "use" concentration and marketing the product in this particular form, the manufacturer can better control the degree of hardness (if any) in the aqueous diluent and can instruct the user to make no further dilution or add any extraneous ingredients. For this reason, the preceding and following discussions of amounts of key ingredients of the composition are generally based upon the total composition, including aqueous diluent, at the "use" concentration.

As is well known in the art, a variety of organic and inorganic agents can increase the viscosity, apparent viscosity, or shear-dependent viscosity (thixotropy) of water. Inorganic types include clays such as bentonite, fumed silica, and the like. Typical of the organic thickeners are a variety of cellulosic (including modified cellulosic) compounds, e.g. hydrophilic cellulosic esters and ethers. Other typical known thickening agents for water are disclosed at column 3, lines 19–40 of the Caughman et al U.S. Pat. No. 3,993,777, the disclosure of which is hereby incorporated by reference. All thickeners do not work with equal effectiveness in this invention, the preferred ones being the cellulosic type, e.g. carboxymethyl cellulose (CMC). A fraction of a percent by weight of such thickeners can increase the viscosity measurement to more than several hundred centipoise. A few percent can thicken water to several thousand centipoise. An important aspect of this thickening is that the teat dip formula is fluid enough for pouring or dipping but still has sufficient viscosity to resist rapid draining or running off from the teat or udder. More than 0.1% by weight of thickener (based on the total composition) provides a thickening effect, while 20 weight-% or more may cause too much thickening. Optimum results are provided with about one part by weight of thickener to each 50-100 parts of water in the end-use composition.

As noted previously, the composition according to the present invention is most suitable for use as a teat dip when in the form of an aqueous solution containing a major amount of thickened water. Even if neutral, softened, distilled, or deionized water is used, adjustment of the pH of teat dip to less than 7.0 is desired. The pH of aqueous solutions of compositions according to the present invention preferably approximate skin pH, e.g. a pH above about 4 but less than about 6.5. A buffer system found by the inventor to be suitable for maintaining the pH at or near 5 (e.g. within about a pH unit) is a citrate-citric acid buffer. Other buffer systems can be used, however, the main requirement for the buffering agent used being that it be physiologically compatible with the skin, compatible with the other ingredients of the composition, and not detrimental with respect to the bactericidal efficacy of the composition. The citrate of the citric acid buffer is preferably the salt of a monovalent metal base such as an alkali metal hydroxide.

The presently preferred pH is about 5 (determined at 23° C.). Efficacy roughly comparable to commercially available iodophor teat dips has been observed at this pH. Such efficacy is difficult to explain in view of the EDTA studies cited previously, but is nevertheless believed to have been substantiated by the presently available data from tests conducted in the course of developing this invention. Although this invention is not bound by any theory, the aminocarboxylic-type chelating agent and the anionic surfactant may, it is felt, cooperate at a pH below 7.

Test data suggest that the amount of anionic sanitizer (by weight on a dry basis) can be effective when it exceeds the amount of aminocarboxylic chelating agent. However, it is presently preferred that the ratio of anionic surfactant to chelating agent not exceed about 5:1. It is believed that the "use" concentration of each of the two ingredients in the anionic surfactant/chelate combination is particularly important. To avoid excessive expense, it is preferable to keep the use concentrations of each ingredient below about 5% by weight (preferably below 4 weight-%) of the composition and the combined concentration of "active" (antibacterial) ingredients below about 10% by weight. At the present time, there appears to be no advantage to exceeding these use concentrations. However, there appears to be no absolute theoretical upper limit on anionic surfactant and chelate concentration so long as one stays generally within the limits of water solubility. On the other hand, dilute solutions containing less than the previously described ranges of use concentrations—for example, the very low use concentrations typically contemplated for hard surface cleaning—may fail to provide an adequate short-term biocidal effect. The risk of failure is believed to be particularly great if the anionic surfactant concentration were to fall below about a half a percent by weight. On a dry solids basis, the anionic surfactant makes up about 3 to 40 weight-% of the composition; more typically 7-30%. The range of dry solids percentages for the chelating agent is similar.

As is known in the art of bactericidal compositions, colorants (e.g. dyes or pigments), odorants, extenders, diluents, surfactants, and other non-essential or optional ingredients can be included in teat dip formulas and thus can be utilized (if desired) in compositions of this invention. Colorants are particularly desirable for aesthetic reasons and are also added for convenience in identifying a product from among a number of products which a dairy farmer may have in the milk-house. As noted previously, other "active" ingredients (biocides, bacteriostats, etc.) can be included in the teat dip, so long as they do not detract from the activity of the anionic surfactant/chelating agent combination. On a dry solids basis, any additional "active" ingredients, if present, will normally be used in amounts smaller than 5 or 10% by weight, e.g. up to 1 or 2%. On a use concentration basis, this range would be roughly two orders of magnitude smaller, e.g. up to 0.1 or 0.2%. The optional "inert" ingredients other than extenders or diluents (e.g. surfactants, including defoamers and cleaners; colorants; and odorants), if suitable for use in the invention, can be included to an extent of about 30 or 40 weight-% on a dry basis, more preferably less than 20 weight-% on a dry basis and less than 0.4% (e.g. less than 0.2%) on a use basis. Suitable diluents and extenders can be present in a wide variety of concentrations (e.g. as replacements for portions of the aqueous phase), so long as the desired use concentrations of the principal active ingredients are not affected.

Compositions according to the present invention have been found to be particularly effective when used as a teat dip, though spraying or swabbing onto the teats might be expected to have somewhat similar bactericidal effects if the contact time and teat skin coverage are about the same. Preferably, the teats of the animal are dipped in a reservoir or receptacle containing a thickened aqueous teat dip of the present invention with the excess being then allowed to drip freely when the source is removed. The high viscosity of the teat dip ensures a contact time greater than a second, e.g. 15 seconds to 15 minutes or longer—in some instances, until the residue of the teat dip is rinsed off. In the teat dip approach, the "use" concentrations of key ingredients of compositions of this invention are preferably used, as explained previously. As also explained previously, pre-dilution to or preselection of the "use" concentration by the manufacturer of the teat dip is preferred. Thus, in the following non-limiting Examples, wherein all parts and percentages are by weight unless otherwise indicated, the exemplary formulations are suitable for use at full strength and are not to be diluted.

EXAMPLES 1–5

In accordance with this present invention, five formulations (Examples 1 through 5) were made up with different levels of linear alkyl benzene sulfonate. The amount of glycerine was the same for Examples 1–4, but Example 5 had an increased amount. The amount of water (quantity sufficient to 100% by weight) varied from 86.762 parts by weight to 91.709 parts by weight. The pH of all five completed formulas was 5.0.

The five formulas are set forth below.

TABLE 1

| Ingredients | Ex. 1 | Ex. 2 | Ex. 3 | Ex. 4 | Ex. 5 |
|---|---|---|---|---|---|
| Linear alkyl benzene sulfonate | 3.500 | 2.500 | 1.500 | 0.500 | 2.000 |
| 50% NaOH | 0.860 | 0.614 | 0.369 | 0.123 | 0.100 |
| EDTA, disodium salt | 1.000 | 1.000 | 1.000 | 1.000 | 1.000 |
| Glycerine | 5.000 | 5.000 | 5.000 | 5.000 | 8.000 |
| REWODERN S-1333* | — | — | — | — | 0.250 |
| Carboxymethyl cellulose | 1.000 | 1.000 | 1.000 | 1.000 | 1.500 |
| Citric acid | 0.100 | 0.100 | 0.100 | 0.100 | 0.124 |
| Sodium citrate | 0.400 | 0.400 | 0.400 | 0.400 | 0.100 |
| Colorant | 0.018 | 0.018 | 0.018 | 0.018 | 0.014 |
| 2-bromo-2-nitropropane-1,3-diol | 0.150 | 0.150 | 0.150 | 0.150 | 0.150 |
| Water | 87.972 | 89.218 | 90.463 | 91.709 | 86.762 |

*Trademark for polyfunctional anionic surfactant (manufactured by Rewo Chemical, Inc., Farmingdale, L.I., New York).

In a comparison study with a reference sample (the product of Example 5 less the EDTA salt), it would appear that there is a slight incompatibility between the alkyl benzene sulfonate and the 2-bromo-2-nitropropane-1,3-diol. The addition of EDTA to the system appeared not only to overcome such incompatibility but substantially enhanced the overall performance of the teat dip.

The effectiveness of the product of Example 5 was compared against the effectiveness of a number of different commercially available or known teat dip products. The results of this comparison are summarized in Table 2.

Although data is available regarding the effectiveness of the commercially available products against gram negative organisms such as *Pseudomonas aeruginosa*, such data are not available for the product of Example 5. Accordingly, the data in Table 2 are limited to *S. aureus* and *S. agalactiae*.

TABLE 2
COMPARATIVE EFFECTIVENESS OF PRODUCT OF EXAMPLE 5 AND VARIOUS PROPRIETARY TEAT DIP PRODUCTS

| Product | Active Ingredient Type | % Active Ingredient | Staph. aureus Geometric Mean No. Recovered | Reduction from Control % | Reduction from Control −Log | Strept. agalactiae Geometric Mean No. Recovered | Reduction from Control % | Reduction from Control −Log |
|---|---|---|---|---|---|---|---|---|
| Control | | | 3,504,500 | | | 3,184,000 | | |
| A | Iodophor | 1.0 | 3 | 99.99 | 6.06 | 3 | 99.99 | 6.03 |
| B | Iodophor | 1.0 | 9 | 99.99 | 5.59 | 19 | 99.99 | 5.23 |

TABLE 2-continued
COMPARATIVE EFFECTIVENESS OF PRODUCT OF EXAMPLE 5 AND VARIOUS PROPRIETARY TEAT DIP PRODUCTS

| | | | | Staph. aureus | | | Strept. agalactiae | | |
|---|---|---|---|---|---|---|---|---|---|
| | | | Geometric | | | | Geometric | | |
| | Active Ingredient | % Active | Mean No. | Reduction from Control | | | Mean No. | Reduction from Control | |
| Product | Type | Ingredient | Recovered | % | −Log | | Recovered | % | −Log |
| C | Iodophor | 0.5 | 7 | 99.99 | 5.69 | | 8 | 99.99 | 5.61 |
| D | Sodium Hypochlorite | 4.2 | 3 | 99.99 | 6.06 | | 1 | 99.99 | 6.51 |
| E | Sodium Dichloro-S-triazinetrione | 0.6 | 35 | 99.99 | 5.00 | | 16 | 99.99 | 5.31 |
| F | Quat. Ammonium Chloride | 0.18 | 371 | 99.99 | 3.97 | | 26 | 99.99 | 5.09 |
| G | Chlorohexidine | 0.5 | 1,252 | 99.96 | 3.46 | | 25 | 99.99 | 5.11 |
| H | Hexachlorophene | * | 600,395 | 82.87 | 0.76 | | 699,715 | 78.02 | 0.65 |
| I | Cetyl Pyridium Chloride | 0.2 | 2,043 | 99.94 | 3.23 | | 655 | 99.98 | 3.69 |
| J | 8-Hydroxy Quinoline Sulfate | 0.1 | 251,530 | 92.82 | 1.14 | | 5,165 | 99.83 | 2.80 |
| K | Pine Oil | * | 94,205 | 97.31 | 1.57 | | 138,970 | 95.64 | 1.36 |
| L | 2-Bromo-2-Nitropropane-1,3-Diol | 0.2 | 24,497 | 99.30 | 2.15 | | 46,054 | 98.55 | 1.85 |
| Product of Ex. 5 | | | | | | | | | |
| | 2-Bromo-2-Nitropropane-1,3-Diol | 0.15 | 20 | 99.99 | 5.24 | | 5 | 99.99 | 5.8 |

*Hexachlorophene and pine oil were presumably the respective active ingredients in these products.

According to the results in Table 2, the product of Example 5 is equally as effective as Iodophor preparations containing 1.0% iodine, against S. aureus and S. agalactiae, i.e. product A and B, and is equally effective as 4.2% sodium hypochlorite, i.e. product D, and a product containing 0.6% sodium dichloro-S-triazinetrione, i.e. product E. It will be noted that the quaternary ammonium chloride based products, i.e. products F and I, were less effective than the active halogen products. The remainder of the products, i.e. products H, J and K were relatively ineffective as a teat dip. It will further be noted that product L containing a higher level of 2-bromo-2-nitropropane-1,3-diol than the product of Example 5 was less effective than Example 5. The difference in performance between product L and the product of Example 5 is believed to result from the inclusion of the anionic surfactant/EDTA salt combination in the product of Example 5.

In summary, the product of Example 5 combines the mildness of a non-halogen teat dip with the effectiveness of the halogen type products, offering a combination of properties hitherto unavailable to dairy farmers. Furthermore, the iodine contamination of milk is not possible with the Example 5 formulation.

EXAMPLES 6-9

Additional Examples similar to Examples 1-5 are set forth below. The pH was 5.0 for all four additional Example formulations. All amounts in the following Table are in parts by weight.

| Ingredients | Ex. 6 | Ex. 7 | Ex. 8 | Ex. 9 |
|---|---|---|---|---|
| Linear alkyl benzene sulfonate | 2.0 | 3.0 | 3.5 | 4.0 |
| 50% NaOH | 0.193 | [Q.S. (quantity sufficient) to pH 5] | | |
| EDTA, disodium salt | 1.0 | 1.5 | 1.75 | 2.0 |
| Glycerine | 8.0 | 8.0 | 8.0 | 8.0 |
| Carboxymethyl cellulose | 1.5 | 1.5 | 1.5 | 1.5 |
| 50% Citric acid | 0.397 | 0.397 | 0.397 | 0.397 |
| "REWODERM" (see Example 5) | 0.25 | 0.25 | 0.25 | 0.25 |
| Color (F, D, and C No. 1) | 0.014 | 0.014 | 0.014 | 0.014 |
| 2-bromo-2-nitropropane-1,3-diol | 0.15 | 0.225 | 0.26 | 0.3 |
| Water | [Q.S. (quantity sufficient to pH 5] | | | |

EXAMPLES 10-12

The following general formulations illustrate the use of NTA, HEDTA, and CDTA in place of EDTA. The terms NTA, HEDTA, and CDTA have the structures shown subsequently.

| Ingredients | Parts by Weight |
|---|---|
| Aminocarboxylic-type chelating agent | 1.0 |
| Linear alkyl benzene sulfonate | 2.0 |
| 50% NaOH | Q.S. to pH 5.0 |
| Glycerine | 8.0 |
| Carboxymethyl cellulose | 1.5 |
| 50% Citric acid | 0.397 |
| "REWODERM" (see Example 5) | 0.25 |
| Color (F, D, and C No. 1) | 0.014 |
| 2-bromo-2-nitropropane-1,3-diol | 0.15 |
| Water | Q.S. to 100 |
| pH | 5.0 |

The aminocarboxylic-type chelating agents used in these Examples were as follows:

| Example | Agent | Formula |
|---|---|---|
| 10 | HEDTA | 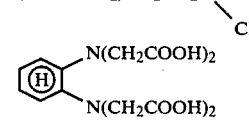 |
| 11 | CDTA | |
| 12 | NTA | $N(CH_2COOH)_3$ |

EXAMPLE 13

This Example illustrates a teat dip formula which does not contain the preferred nitroalkanol (2-bromo-2-nitropropane-1,3-diol) or any of its analogs.

| Ingredients | Weight % |
|---|---|
| Linear alkyl benzene sulfonate (97% active) | 2.00 |
| 50% NaOH | 0.10 |
| EDTA, tetrasodium salt | 1.00 |
| Glycerine | 8.00 |
| Carboxymethyl cellulose | 1.50 |
| Citric acid | 0.124 |
| Sodium citrate | 0.10 |

-continued

| Ingredients | Weight % |
| --- | --- |
| Color (F, D, C Blue No. 1) | 0.0144 |
| "REWODERM" S-1333 (trade designation | 0.25 |
| Water | Q.S. to 100% |
| pH | about 5.0 |

I claim:

1. A method for killing mastitis-causing organisms on an animal's teats, wherein control over the organisms can be obtained in less than 15 minutes, said method comprising the step of treating the teats of the animal with a composition containing a major amount of water, having a pH above 4 and below 6.5 at 23° C., and consisting essentially of:
   (a) at least about 0.1% by weight of an aminocarboxylic acid or aminocarboxylate chelating agent having a calcium chelate stability constant of at least about 6;
   (b) at least 0.5% by weight of an anionic surfactant uniformly distributable in water and having the general formula $LSO_x^{\ominus}N^{\oplus}$ wherein L is organic, x is 3 or 4, and $N^{\oplus}$ is a topically acceptable cation; and
   (c) up to about 98% by weight of an aqueous diluent; said components (a) and (b) being uniformly distributed through said aqueous diluent.

2. A method according to claim 1 wherein said chelating agent is selected from the topically acceptable salts of a nitrilopolyacetic acid selected from the group consisting of EDTA, CDTA, HEDTA, and NTA.

3. A method according to claim 1 wherein said chelating agent comprises an ethylenediaminetetraacetate of the formula $H_m^+M_{4-m}^+EDTA^{-4}$, wherein
   $EDTA^{-4}$ represents the ethylenediaminetetraacetate anion,
   $M^+$ represents a topically acceptable cation, and
   m represents an integer from 0 to 3.

4. A method according to claim 3 wherein said $M^+$ is an alkali metal cation.

5. A method according to claim 4 wherein said ethylenediaminetetraacetate comprises the disodium salt of ethylenediaminetetraacetic acid.

6. A method according to claim 2 wherein said composition comprises 80–92% by weight of water, said carboxylate salt being dissolved in said water.

7. A method according to claim 2 further comprising a buffering agent to stabilize the pH of said composition at about 5, and an effective amount of an emollient.

8. A method according to claim 1 wherein said anionic surfactant is selected from the group consisting of linear alkylbenzene sulfonic acid and its topically acceptable salts.

9. A method according to claim 1, wherein said composition is a teat dip further comprising:
   (d) 0.1 to about 10% by weight of emollient;
   (e) a thickening amount of a water-thickening agent; and
   (f) a buffering amount of a buffer, sufficient to provide a buffered pH in the said pH range.

10. A method according to claim 1 wherein said treating comprises the step of dipping the teats in a reservoir of said composition.

11. A method according to claim 9, wherein said treating comprises the step of dipping the teats in a reservoir of said composition.

12. A method according to claim 1, wherein said composition consists essentially of:
   disodium or tetrasodium ethylenediaminetetraacetate in an amount of about 1.0 to about 2.0% by weight;
   $C_9$ to $C_{18}$-linear alkyl-benzene sulfonate in an amount of from 0.5 to 3.5% by weight;
   glycerine in an amount of 0.1 to 10% by weight;
   a cellulosic thickener in an amount of more than 0.1% but less than 20% by weight;
   water in an amount of from about 80 to about 92% by weight;
   a citric acid—citrate buffer in an amount sufficient to stabilize said pH; and
   0–0.4 by weight of colorants, odorants, and any additional surfactants.

13. A method according to claim 1 comprising the step of spraying the teats of the animal with the said composition.

* * * * *